United States Patent [19]
Herb

[11] Patent Number: 4,636,123
[45] Date of Patent: Jan. 13, 1987

[54] EXPANSION ANCHOR ASSEMBLY

[75] Inventor: Armin Herb, Peissenberg, Fed. Rep. of Germany

[73] Assignee: Hilti Aktiengesellschaft, Furstentum, Liechtenstein

[21] Appl. No.: 681,023

[22] Filed: Dec. 13, 1984

[30] Foreign Application Priority Data

Dec. 22, 1983 [DE] Fed. Rep. of Germany ....... 3346537

[51] Int. Cl.$^4$ ............................................. F16B 13/06
[52] U.S. Cl. ......................................... 411/55; 411/60
[58] Field of Search ..................... 411/49, 50, 51, 52, 411/53, 54, 55, 56, 57, 60, 63, 64, 65, 66, 67, 68

[56] References Cited

U.S. PATENT DOCUMENTS

| | | | |
|---|---|---|---|
| 406,565 | 5/1889 | Church | 411/53 |
| 626,040 | 7/1889 | Rowlands | 411/54 |
| 681,817 | 3/1901 | Smith | 411/53 |
| 694,345 | 3/1902 | Bennett | 411/65 |
| 1,959,439 | 5/1934 | McIntosh | 411/53 |
| 2,319,376 | 5/1943 | Wallace | 411/53 |
| 2,381,050 | 8/1945 | Hardinge | 411/55 X |
| 2,642,768 | 6/1953 | Ogburn | 411/53 |
| 2,783,673 | 3/1957 | Lewis et al. | 411/53 |

FOREIGN PATENT DOCUMENTS

| | | | |
|---|---|---|---|
| 1297330 | 5/1962 | France | 411/55 |
| 682562 | 11/1952 | United Kingdom | 411/53 |
| 932693 | 7/1963 | United Kingdom | 411/55 |
| 2048419 | 12/1980 | United Kingdom | 411/67 |

Primary Examiner—Thomas J. Holko
Attorney, Agent, or Firm—Toren, McGeady & Goldberg

[57] ABSTRACT

An expansion anchor assembly includes an expansion sleeve formed at least in part by axially extending extension sections, an expansion body and an anchor rod attached to the expansion body. By pulling the expansion body into the end of the sleeve formed by the expansion sections, the sections are spread radially outwardly. An axially extending part of the outside surface of the expansion body is formed by a plurality of outwardly tapering axially extending and circumferentially adjacent convex surfaces having an arc shape in the direction transverse to the axial direction of the expansion body. The radius of curvature of each arc-shaped convex surface is the same over its axial length. Each expansion section of the sleeve has an axially extending radially inner concave surface corresponding to one of the arc-shaped convex surfaces on the expansion body.

11 Claims, 8 Drawing Figures

U.S. Patent  Jan. 13, 1987  4,636,123
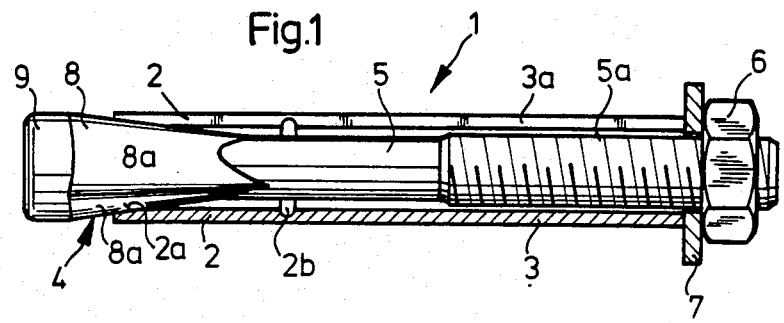
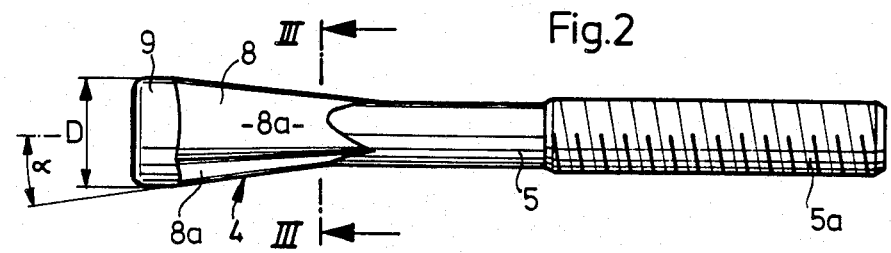
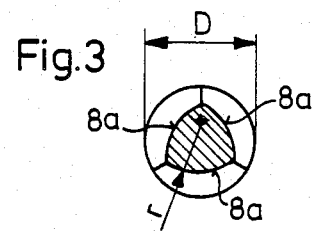 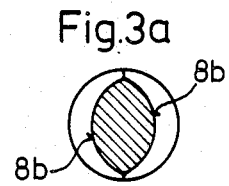 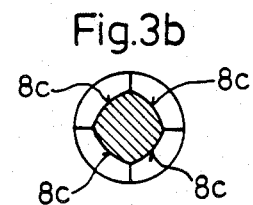
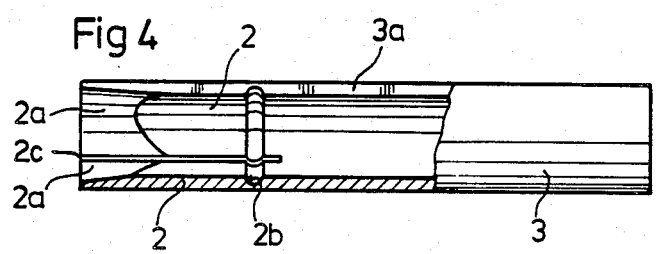 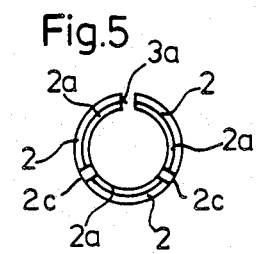
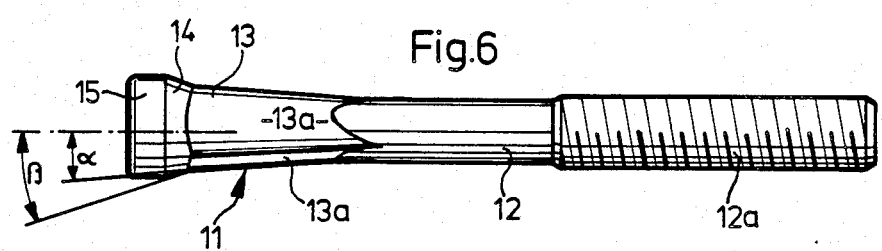

EXPANSION ANCHOR ASSEMBLY

BACKGROUND OF THE INVENTION

The present invention is directed to an expansion anchor assembly made up of an expansion sleeve, an expansion body and an anchor rod secured to the expansion body so that the rod serves for the attachment of a load to the assembly and also axially displaces the expansion body through the sleeve for displacing at least a part of the sleeve radially outwardly into anchoring engagement with the surface of a borehole into which the assembly is inserted.

Known expansion anchor assemblies are secured in a borehole by pulling a generally conically shaped expansion body in the direction out of the borehole. The pulling action is provided by anchor rods secured to the expansion body. In the expanding or spreading of the expansion sleeve, the expansion body moves along the inside surface of the sleeve and presses the sleeve radially outwardly into anchoring engagement with the surfaces of the borehole. As the expansion body is drawn into the expansion sleeve, at least an axially extending portion of the sleeve is deformed because of the changing diameter, that is, the sleeve is expanded or spread due to the conical shape of the expansion body. As the expansion body is drawn into the sleeve the surface of the sleeve may become jammed on the expansion body so that a displacement of the expansion sleeve together with the expansion body without obtaining anchoring values may take place. The radial displacement of the expansion sleeve during the anchoring process also produces a very high tensile stress in the anchor rod. Another considerable disadvantage when such jamming action occurs is that after spreading of the anchoring assembly is, in most instances, not attainable.

SUMMARY OF THE INVENTION

Therefore, it is the primary object of the present invention to provide an expansion anchor assembly where the expansion body can be drawn into the expansion sleeve at low tensile forces and without any risk of jamming whereby an improved after-spreading of the assembly is obtainable.

In accordance with the present invention, the expansion body has an axially extending outside shape made up of a plurality of circumferentially adjacent arc-shaped convex surfaces. Each arc-shaped surface has the same radius of curvature along a significant axial length of the expansion body. The expansion sleeve has an axially extending expansion section corresponding to each of the arc-shaped surfaces on the expansion body and the inside surface of the expansion sections are concave and provided with an arc-shaped surface corresponding to the similar surface on the expansion body.

Due to the same radius of curvature of the arc-shaped surfaces extending axially along the length of the expansion body and the corresponding shape of the inside surfaces of the expansion sections on the expansion sleeve, no deformation and, as a result, no jamming of the expansion sections occurs as the expansion body is drawn into the sleeve. Instead, the expansion body can be pulled into the end of the expansion sleeve formed by the expansion sections whereby there is small resistance to radial displacement and the expansion sections are displaced radially outwardly into tightly anchoring engagement with the surface of the borehole. In this way, a uniform distribution of the expansion pressure is afforded over the axial length of the expansion sections of the sleeve.

Another advantage of the present invention is that the expansion sections are secured in the borehole against any rotational movement relative to the expansion body, because of the non-circular cross-section of the inside surface of the expansion sections of the sleeve. The expansion sections of the sleeve can be secured together by a sleeve section secured to and extending axially away from the expansion sections. It is also possible to assembly the expansion sections into a sleeve-like section using a ring or some similar retaining member.

The expansion body can be secured to the anchor rod in various ways. The expansion body can be formed monolithically with the anchor rod with the anchor rod having an external thread at its end opposite the expansion body for the attachment of a load. Alternatively, the expansion body can have a continuous thread bore engageable with the anchor rod in the form of a threaded member for effecting relative axial displacement.

To facilitate production, it is preferable to shape all of the arc-shaped surfaces so that they have the same radius of curvature.

Basically, it would be possible to provide two or more arc-shaped surfaces on the expansion body with a corresponding number of expansion sections on the sleeve. In a preferred embodiment, the expansion body is provided in the circumferential direction with three arc-shaped surface to assure trouble-free protection against any relative turning of the parts of the assembly as well as effective distribution of the expansion force. Preferably the arc-shaped surfaces are formed along a circular arc which also aids in improving the distribution of the expansion force.

The preferred dimension of the arc-shaped surfaces for achieving the above advantages, involves selecting the radius of curvature as half of the largest diameter of the expansion body. Such a dimensional arrangement leads to a stepless transition from the peripheral contour of the arc-shaped surfaces to the largest diameter of the expansion body so that it is possible to achieve a maximum possible length of the peripheral surfaces affording the spreading of the expansion sections of the sleeve. This embodiment is particularly advantageous in an expansion anchor assembly where the expansion body and the anchor rod are formed monolithically so that the arc-shaped surfaces of the expansion body taper outwardly from the end of the anchor rod. In such an arrangement, it is suitable to assemble the expansion sections into a sleeve-like arrangement by means of rings or the like.

Further, in accordance with the present invention the apices of the arc-shaped surfaces form an angle in the range of 5° to 20° with respect to the axis of the expansion body. This angular characteristic assures, on one hand, the effective availability of forces for drawing the expansion body into the expansion sleeve, and, on the other hand, the advantage of a self-locking connection between the expansion sections on the sleeve and the arc-shaped surfaces on the expansion body. In this way, a favorable correlation is provided between the axial displacement of the expansion body and the extent of radial displacement of the expansion sections.

In particular for utilization in soft receiving material or in receiving material subject to fracturing, a conical zone expanding in the setting direction with an angle between the conical contour and the axis of the expansion body, exceeding the apex angle, adjoins the peripheral contour in the setting direction according to a further feature of the invention. If further displacement of the expansion body opposite to the setting direction occurs, the expansion anchor assembly being under load, for instance, due to cracks occurring in the receiving material, then the conical zone slides into the expansion sections tightened in the installation bore, causing a deformation to occur during expansion. Such deformation opposes a higher resistance to drawing the expansion body into the expansion sleeve, as is well known for conventional expansion bodies with a conically shaped peripheral surface. The conical zone causes an increase in the locking value and prevents, due to the increased resistance to the drawing in operation, a pulling of the expansion body out of the expansion sections. To obtain this effect it is sufficient to have the angle of the cone contour exceed the apex angle only by a few degrees, 20° at a maximum.

The various features of novelty which characterize the invention are pointed out with particularity in the claims annexed to and forming a part of this disclosure. For a better understanding of the invention, its operating advantages and specific objects attained by its use, reference should be had to the accompanying drawing and descriptive matter in which there are illustrated and described preferred embodiments of the invention.

BRIEF DESCRIPTION OF THE DRAWING

In the drawing

FIG. 1 is a view extending in the axial direction of an expansion anchor assembly embodying the present invention, with a portion of the assembly shown in section;

FIG. 2 is a view of the anchor rod and expansion body as illustrated in FIG. 1;

FIG. 3 is a sectional view taken along the line III—III of the expansion body in FIG. 2;

FIG. 3a is a sectional view, similar to FIG. 3, through an expansion body of a different cross-sectional shape;

FIG. 3b is a sectional view similar to FIGS. 3 and 3a through another expansion body of a different cross-sectional shape;

FIG. 4 is an axially extending view of an expansion sleeve with expansion sections as illustrated in FIG. 1 and shown partially in cross-section;

FIG. 5 is an end view of the expansion sleeve viewed from the end formed by the expansion sections; and FIG. 6 is another embodiment of the combined anchor rodexpansion body of the expansion anchor assembly.

DETAILED DESCRIPTION OF THE INVENTION

In FIG. 1 an expansion anchor assembly is shown for insertion into a borehole. As viewed in FIG. 1 the left-hand ends of the various parts of the assembly are the leading ends, that is, the ends inserted first into the borehole while the right-hand ends are the trailing ends which extend into or out of the surface of the receiving material in which the borehole is formed. The expansion anchor assembly is made up of a sleeve-like member formed by expansion sections 2 extending from the leading end for a portion of the axial length of the sleeve-like member toward the trailing end and by a sleeve section 3 securing the expansion sections together with the sleeve section extending axially from the trailing ends of the expansion sections to the trailing end of the sleeve-like member. Axially extending slits 2c separate each of the expansion sections. In addition the assembly includes an expansion body 4 fixed to the leading end of an anchor rod 5 with the trailing end of the anchor rod extending axially out of the trailing end of the sleeve section 3. Anchor rod 5 is threaded for a section 5a extending from its trailing end and a nut 6 is threaded onto the threaded section 5a. A washer 7 is located between the nut and the trailing end of the sleeve section 3. As shown in FIGS. 1 and 2, the expansion body 4 has an axially extending peripheral section 8 tapering outwardly in the direction toward the leading end of the expansion body. At the larger diameter end of the peripheral section 8, a cylindrical extension 9 having a diameter corresponding to the larger diameter end of the peripheral section forms the leading end of the expansion body. As can be better appreciated in FIG. 3, the peripheral section 8 is formed by three axially extending arc-shaped convex surfaces 8a arranged adjacent one another in the circumferential direction of the expansion body 4. The arc-shaped surfaces 8a intersect one another along a rectilinear line extending for the full axial length of the peripheral section. Each arc-shaped surface has the same radius of curvature along its full axial length. In cross-section, as viewed in FIG. 3, initially the arc-shaped surfaces, transverse to the axial direction, form a triangular-like cross-section with such cross-section gradually changing into a circular cross-section at the ends of the arc-shaped surfaces adjoining the cylindrical extension 9. The radius r of the arc-shaped convex surfaces correspond to half of the largest diameter D of the expansion body, that is, the diameter of the cylindrical extension 9.

In FIG. 3a another embodiment of the expansion body is shown where the peripheral section is formed by two arc-shaped surfaces 8In FIG. 3b there is yet another embodiment where the transverse cross-section of the expansion body has the peripheral section 8 formed by four arc-shaped surfaces 8c. The apex of each of the arc-shaped surfaces 8a, 8b, 8c is inclined at an angle α of about 10° with respect to the axis of the expansion body 4. As can be noted in FIGS. 4 and 5, each expansion section 2 extends angularly in the circumferential direction for an angle of approximately 120°. The radially inner surface 2a of a portion of the expansion sections 2 extending from the leading end of each section is shaped complementary to the arc-shaped convex surfaces 8a and, accordingly, the radially inner surfaces 2a are concave. The sleeve section 3 from the trailing end of the expansion sections 2 to the trailing end of the sleeve-like member forms a longitudinal slit 3a for facilitating the formation of the sleeve-like member and the slit 3a forms a continuation of one of the slits 2c extending to the leading end of the member extending between two adjacent expansion sections 2. At the transition between the expansion sections 2 and the sleeve region 3, the inner surface of the expansion sections are provided with a circumferential recess 2b extending around the inside surface. The recess 2b provides a reduced strength cross-section and thus promotes the radially outwardly directed spreading of the expansion sections during the anchoring operation.

In FIG. 6, an anchor rod 12 with an external threaded section 12a at its trailing end is attached at its leading end to an expansion body 11. The expansion body 11 has an outer peripheral surface 13 tapering outwardly toward the leading end of the expansion body. The peripheral surface 13 is divided into three arc-shaped convex surfaces 13a. The radius of the arc-shaped surfaces 13a, comparable to the small r in FIG. 3 is approximately 10% smaller than half of the larger diameter end of the expansion body 11 formed by the cylindrical extension 15 The larger diameter is comparable to the diameter D in FIG. 3.

The angle $\alpha$ of the apex of the arc-shaped surfaces 13a relative to the axis of the expansion body is approximately 8°. An axially extending frusto-conical section 14 extends axially outwardly from the leading end of the expansion surface 13a. The frusto-conical section forms an angle $\beta$ with respect to the axis of the expansion body 11 which is approximately 15° larger than the angle $\alpha$. The leading end of the frusto-conical section 14 has the same diameter as the cylindrical extension 15 so that a smooth transition is provided.

It is the purpose of the frusto-conical section 14, in the event cracks are present in the receiving material into which the expansion anchor assembly is set, to obtain an increase of the anchoring value as the frusto-conical section enters into the expansion sections 2. As a result, a deformation and resulting jamming of the expansion sections takes place, so that the resistance to drawing the expansion body 11 into the expansion sections 2 increases considerably. The frusto-conical section 14 thus serves at least as a partial block for the movement of the expansion body 11 into the sleeve-like member.

While specific embodiments of the invention have been shown and described in detail to illustrate the application of the inventive principles, it will be understood that the invention may be embodied otherwise without departing from such principles.

I claim:

1. Expansion anchor assembly comprising an axially extending expansion sleeve, an expansion body for radially expanding at least an axially extending part of said expansion sleeve, and an anchor rod connected to said expansion body for axially displacing said expansion body into said expansion sleeve and for attaching a load, said expansion sleeve having a first end and a second end and comprising a plurality of axially extending coextensive slits extending from the first end toward the second end of and dividing said expansion sleeve into a plurality of separate coextensive axially extending expansion sections, each said expansion section having an axially extending radially inner surface and an axially extending radially outer surface, said expansion body having a first end and a second end with said expansion body having a first end and a second end with said second end insertable into the first end of said expansion sleeve so that said expansion body can be displaced axially into said expansion sleeve from the first end toward the second end for radially expanding said expansion sections, said expansion body having a radially outer surface comprised of a plurality of axially extending coextensive expansion surfaces arcuately curved in the direction transverse to the axial direction, said expansion surfaces having axially extending edges with said edges on adjacent said expansion surfaces being being contiguous, and said expansion surfaces tapering outwardly from the axis of said expansion body in the direction from the second ends toward the first end thereof, each said expansion surface being arranged to contact a corresponding said expansion section and an axially extending part of the radially inner surface of said expansion sections commencing at the leading end thereof being concavely arc-shaped transverse to the axial direction of said expansion sleeve and the arc-shape of the axially extending part of the radially inner surface corresponding to the arc-shape of said expansion surfaces on said expansion body, and each of said arc-shaped surfaces on said expansion body has the same radius of curvature along the axial length of said surfaces.

2. Expansion anchor assembly, as forth in claim 1, wherein the radially outer surface of said expansion body is divided into three axially extending arc-shaped surfaces.

3. Expansion anchor assembly, as set forth in claim 1, wherein said arc-shaped surface of said expansion body are formed by an arc of a circle.

4. Expansion anchor assembly, as set forth in claim 3, wherein said arc-shaped surfaces of said expansion body have a radius of curvature corresponding to half of the diameter of the first end of said expansion body.

5. Expansion anchor assembly, as set forth in claim 1, wherein each of said arc-shaped surfaces of said expansion body has an axially extending apex spaced equidistantly from the axially extending edges thereof and said apex extends at an angle in the range of 5° to 20° relative to the axis of said expansion body.

6. Expansion anchor assembly, as set forth in claim 5, wherein said expansion body has an axially extending cylindrical extension extending from the first end thereof toward the second end, a frusto-conical section extending from said cylindrical extension to the adjacent end of said arc-shaped surfaces of said expansion body, and said frusto-conical section tapering outwardly from said arc-shaped surfaces to said cylindrical extension at an angle to the axis of the expansion body which is larger than the angle of the apex of the expansion surfaces to the axis of the expansion body.

7. Expansion anchor assembly, as set forth in claim 1, wherein a longitudinal slot extends in the axial direction of said expansion sleeve from the end of one of said slits closer to the second end of said expansion sleeve to the second end of said expansion sleeve.

8. Expansion anchor assembly, as set forth in claim 1, wherein a circumferentially extending annular recess is formed in the radially inner surface of said expansion sections located closer to the second end of said expansion sleeve.

9. Expansion anchor assembly, as set forth in claim 1, wherein the contiguous axially extending edges of said expansion surfaces extend rectilinearly in the axial direction forming a ridge-like line at the intersection between the contiguous said expansion surfaces with said ridge-like line disposed at an acute angle relative to the axis of said expansion body.

10. Expansion anchor assembly, as set forth in claim 1, wherein said expansion body has an axially extending cylindrical extension of circular cross-section extending from the first end of said expansion body to the adjacent ends of said expansion surfaces with the radius of said cylindrical extension being the same as the radius of said expansion surfaces.

11. Expansion anchor assembly, as set forth in claim 1, wherein the ends of the expansion surfaces closer to the first end of said expansion body form a circular cross-section.

* * * * *